United States Patent
Schmidt

[19]
[11] Patent Number: 5,928,273
[45] Date of Patent: Jul. 27, 1999

[54] COUPLING DEVICE FOR CONNECTING A MEDICAL THERAPY DEVICE TO A SUPPLY

[75] Inventor: Peter Schmidt, Argenbühl-Eisenharz, Germany

[73] Assignee: Schmidt & Lenhardt OHG, Oberstenfeld, Germany

[21] Appl. No.: 09/043,707

[22] PCT Filed: Dec. 6, 1996

[86] PCT No.: PCT/EP96/05466

§ 371 Date: Mar. 25, 1998

§ 102(e) Date: Mar. 25, 1998

[87] PCT Pub. No.: WO97/21412

PCT Pub. Date: Jun. 19, 1997

[30] Foreign Application Priority Data

Dec. 8, 1995 [DE] Germany ............................ 195 45 792
May 10, 1996 [DE] Germany ............................ 196 18 787
Jun. 28, 1996 [DE] Germany ............................ 196 25 945

[51] Int. Cl.$^6$ ...................................................... A61F 7/02
[52] U.S. Cl. ............................................. 607/104; 607/96
[58] Field of Search ...................................... 607/104, 108, 607/96; 403/37–39; 137/625.12, 625.17, 625.18, 625.42

[56] References Cited

U.S. PATENT DOCUMENTS 3,606,890  9/1971  Gilbert ..................................... 607/104
5,411,541  5/1995  Bell et al. ............................... 607/104

FOREIGN PATENT DOCUMENTS 0 039 443  11/1981  Germany .
95/10251   4/1995   WIPO .

*Primary Examiner*—John P. Leubecker
*Attorney, Agent, or Firm*—Notaro & Michalos P.C.

[57] ABSTRACT

A coupling device connects a medical therapy device, such as a therapy cushion, to a supply device. The coupling device includes a coupling part connected to a double hose line and a counter-coupling complimentarily designed to attach to the coupling part and fitted on the supply device. The coupling device further includes a plurality of shut-off valves that, by step-wise movement between the coupling part and counter coupling, selectively open flow paths for supply of different amounts of fluid per unit of time.

7 Claims, 11 Drawing Sheets

COUPLING DEVICE FOR CONNECTING A MEDICAL THERAPY DEVICE TO A SUPPLY

FIELD OF THE INVENTION

This invention relates to a device for regulating the temperature of skin parts of the human body comprising a cushion which can be put on the body and which comprises a liquid channel system having an inlet opening and an outlet opening, a forward flow line connected to the inlet opening, a return flow line connected to the outlet opening, further comprising a supply device provided with a heat-insulated box comprising a cover and a pump connected at it's suction side to the interior of the box, and a supply connection connected to the pump, the supply connection connectable to the forward flow line and means connecting the return flow line to the box.

BACKGROUND OF THE INVENTION

Devices of this kind are known from the WO 95/10251, EP-0039443, U.S. Pat. No. 5,411,541, U.S. Pat. No. 3,807,939, U.S. Pat. No. 5,190,033, DE-3505274. Disadvantageous in the published suggestions is the fact, that only one therapy cushion can be connected with the supply device. In practice there is an urgent need to treat several distanced skin surfaces of the patients with heat and/or cold at the same time. According to the state of the art each cushion would afford an own supply device. Another possibility would be a common forward flow line and a common return flow line for a plurality of cushions with built-in T-junctions. The disadvantage of this possibility would be the fact, that the individual cushions cannot be regulated individually.

SUMMARY OF THE INVENTION

Main object of the invention is to provide a temperature regulating device of the kind mentioned at the beginning, whereby several therapy cushions can be operated by one supply device with temperature regulated liquid and nevertheless individual supply of the cushions with temperature regulated liquid should be possible.

According to an embodiment of the invention the shut-off valves are designed as metering valves, which are assigned to the forward flow lines. The respective shut-off valves can be opened sensitively or continuously, thus the individual cushions can be supplied with different amounts of heat or cold per unit of time. Thereby a differing temperature adjustment for the cushions is indirectly possible. Preferably in the peripheral area of the box the cover of the supply device provides a number of openings equal to the number of supply connections, whereby the openings each show a cross-section minimum equal to the outer cross-section of the return flow lines, so that the return flow lines are easily insertable into the box via the openings. The return flow lines then empty off directly into the box.

As an alternative solution within the bounds of the invention the shut-off valves during coupling of the foward flow lines are designed as automatically opening check valves.

An important development of the invention is, that the liquid channel systems of the several cushions show flow resistances, which are at least nearly proportional to the surfaces of the cushions. Thereby it is managed that in small cushions—i.e. nose- or cheek-cushions—the flow cross-sections are smaller than in large surface cushions—i.e. tigh bandages—thus also the liquid flow rates are at least nearly proportional to the respective cushion sizes.

The invention furthermore provides a coupling device for connecting a coupling part of a double hose line, comprising an inner and an outer hose, with a supply connection. These coupling devices are especially advantageous for connecting the therapy cushions, because each cushion only affords one coupling device which connects the forward flow line as well as the return flow line with the supply device, thus a false connection of the lines is avoided. This coupling device can also be used for the connection of a cushion with the forward and return flow lines, so that double hose lines of differing length can be used, and it is also possible to connect double hose lines with one another or with devices.

BRIEF DESCRIPTION OF THE DRAWINGS

The invention is described in detail for instance in connection with the drawings.

DETAILED DESCRIPTION OF THE INVENTION

Figure 1:
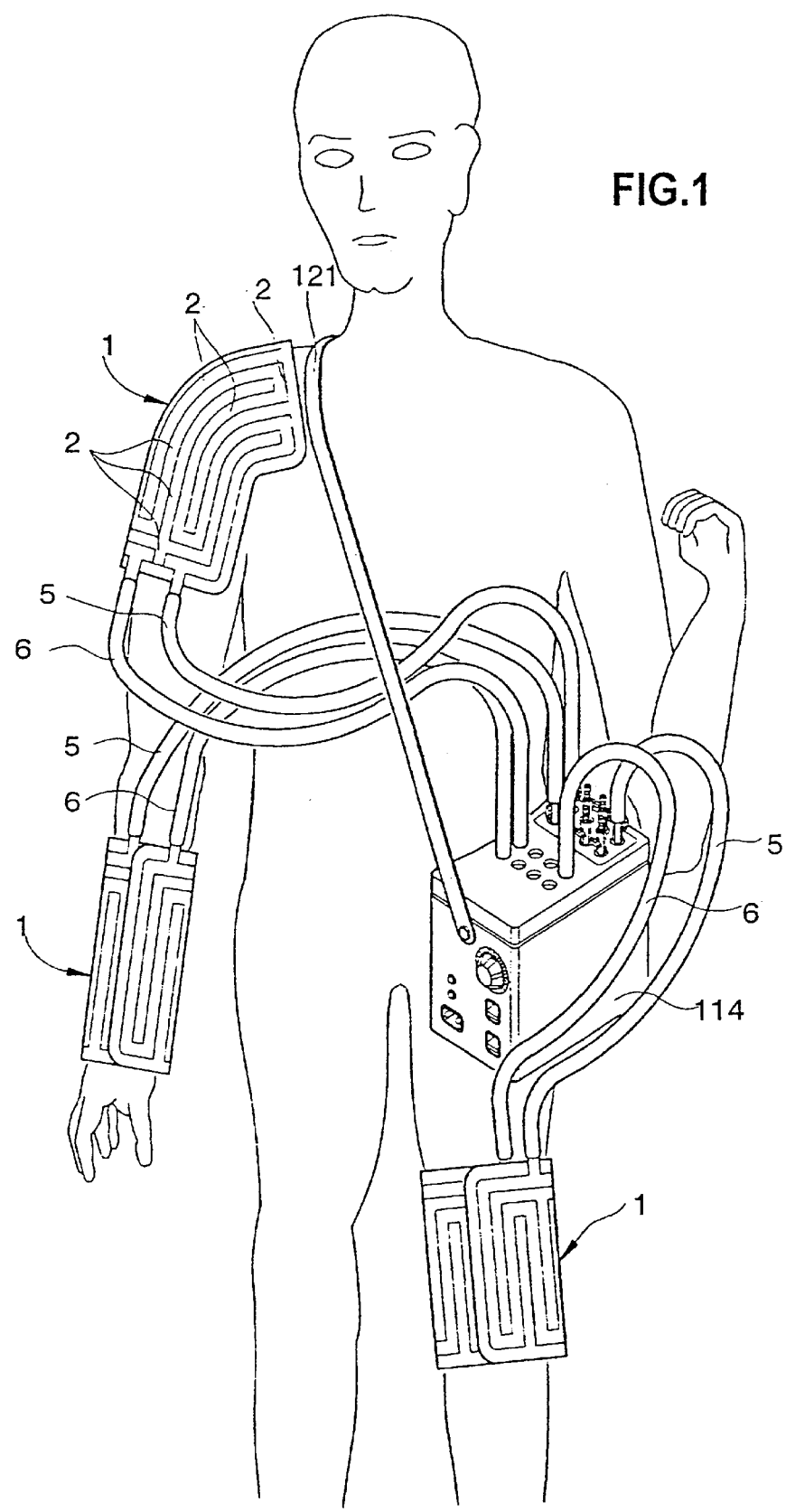
FIG. 1 is a view on a supply device with several simultaneously connected cushions, which are connected to the supply device via separate forward and return flow lines.
Figure 2:
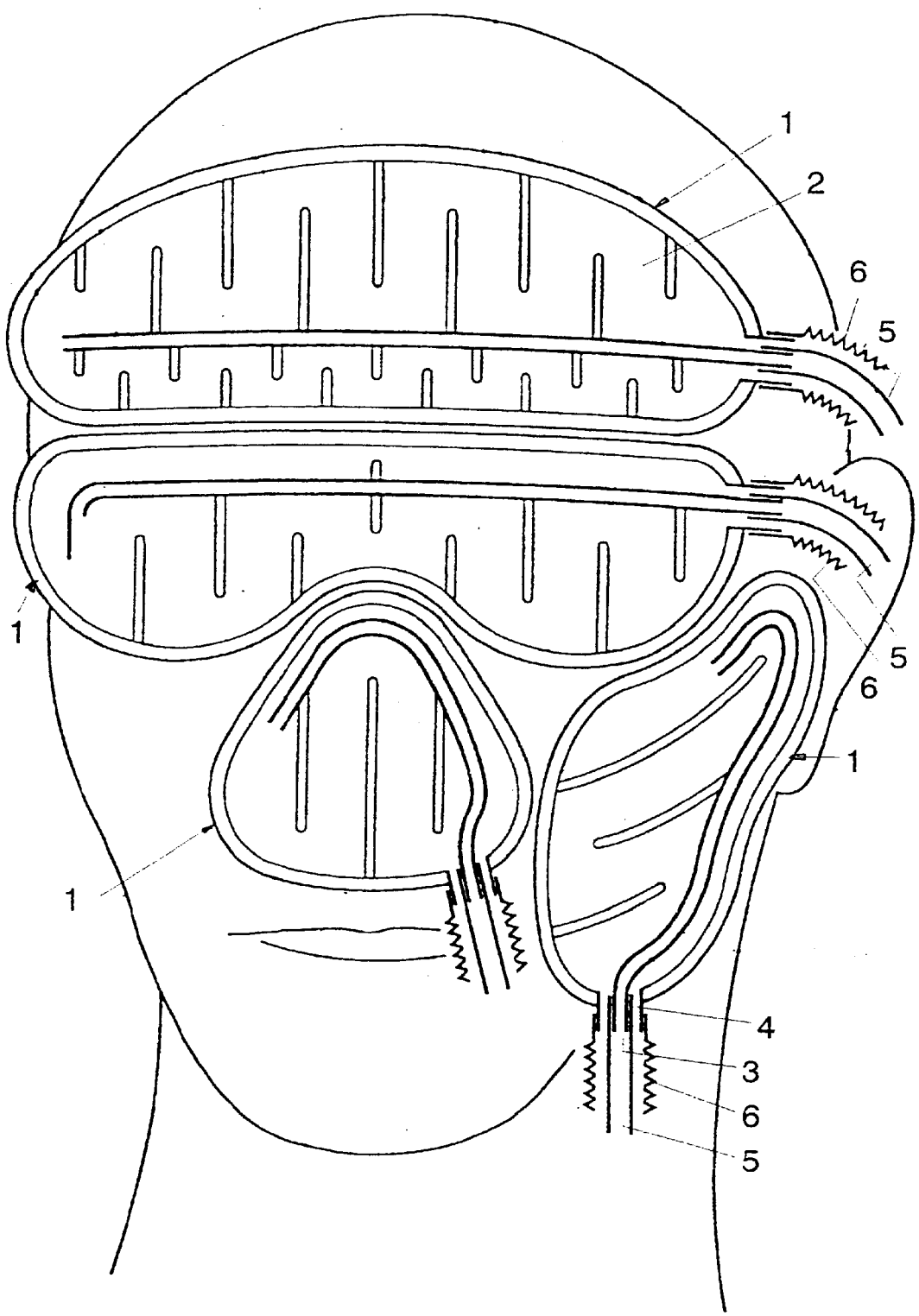
FIG. 2 is a view on several smaller cushions at the head of a patient, with the forward flow lines being led coaxially in the return flow lines, so that each cushion can be connected to the supply device via a sole double hose line.
Figure 4:
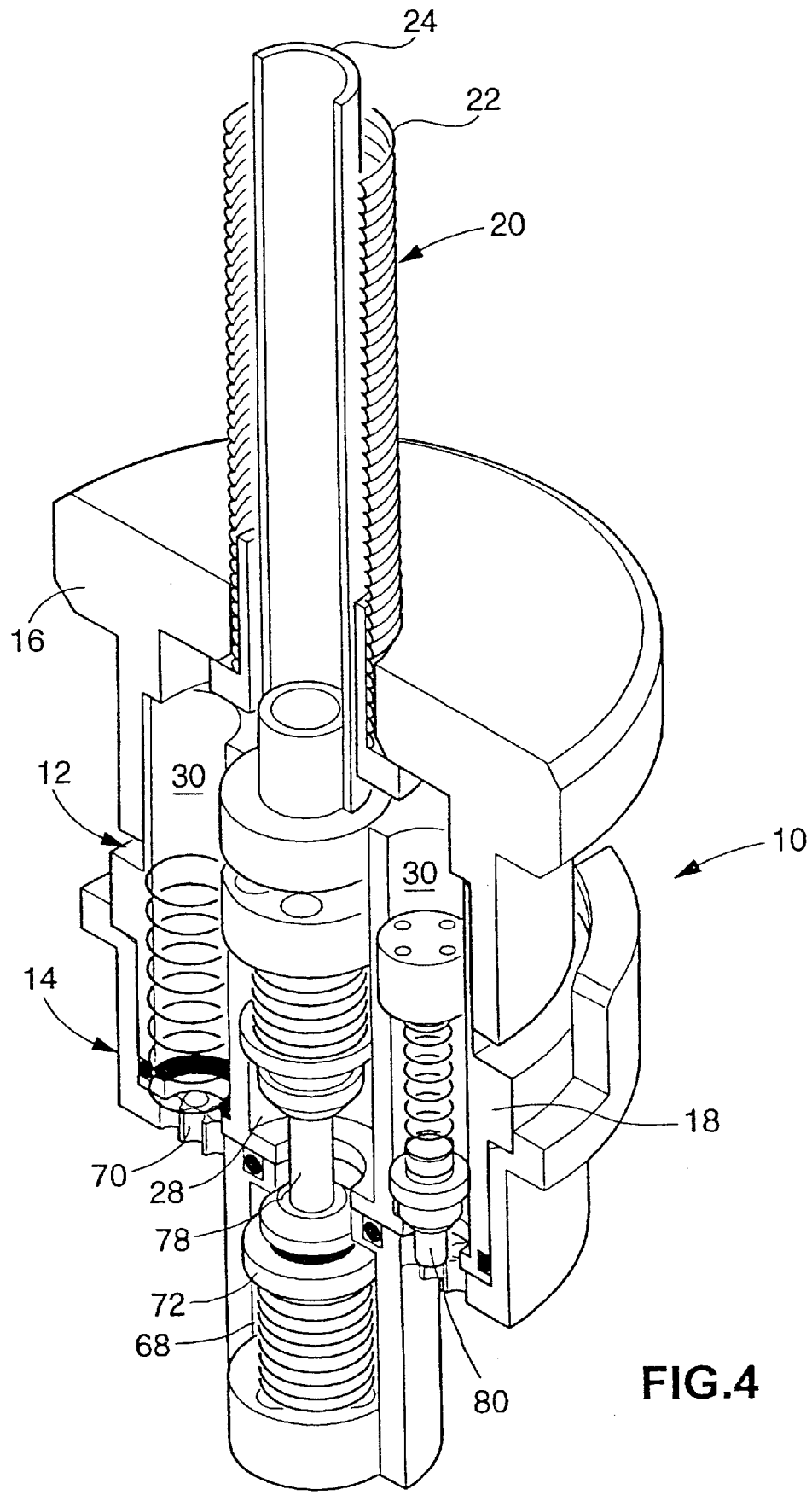
FIG. 4 shows a coupling device, which is used with a supply device for cushions with coaxial in- and outlet openings according to FIG. 2, FIGS. 5–7 show parts of the coupling device according to FIG. 4.
Figure 5:
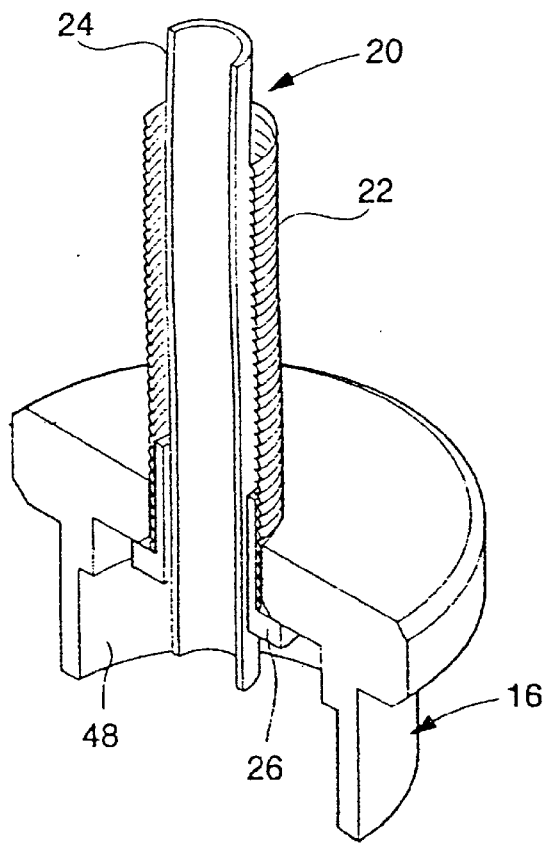
Figure 6:
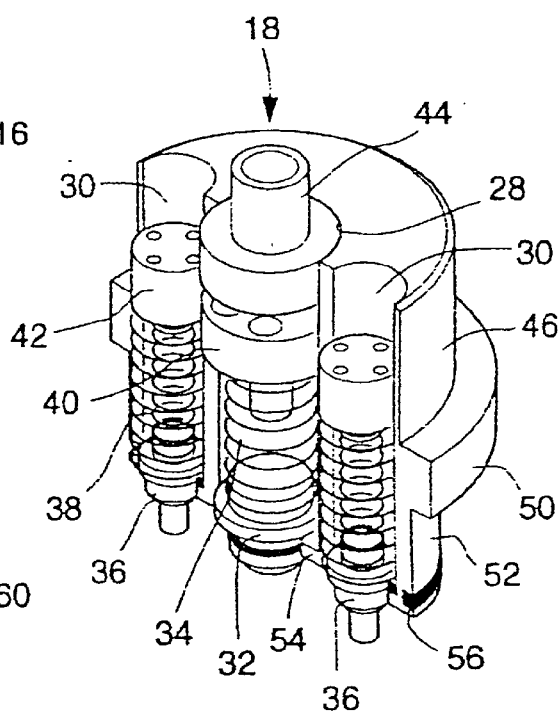
Figure 7:
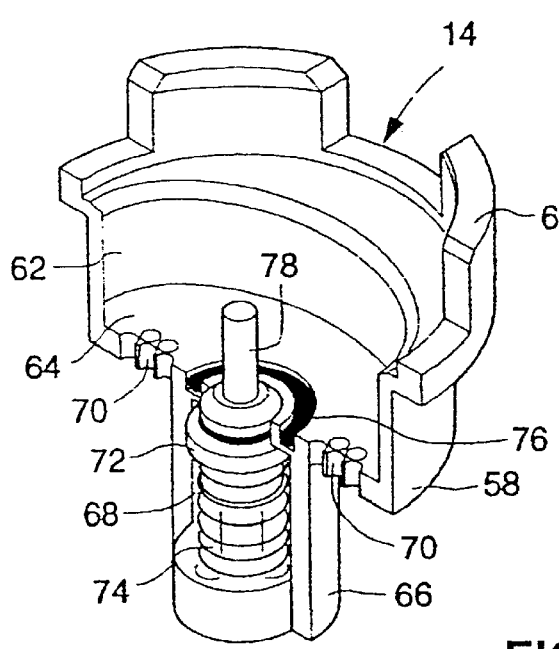

The device for temperature regulation of skin parts comprises several cushions 1, each of them comprising a liquid channel system 2 with an inlet opening 3 and an outlet opening 4 as well as a forward flow line 5 and a return flow line 6. According to FIG. 1 the forward and return flow lines 5, 6 are connected separately to a supply device 114. In the embodiment according to FIG. 2 the forward and return flow lines 5, 6 are coaxially arranged and form a double hose 20 (FIG.4).

The forward and return flow lines 5, 6 can be detachably put on respective connection fittings of the cushions 1 or can be connected fix to the cushion.

Figure 3:
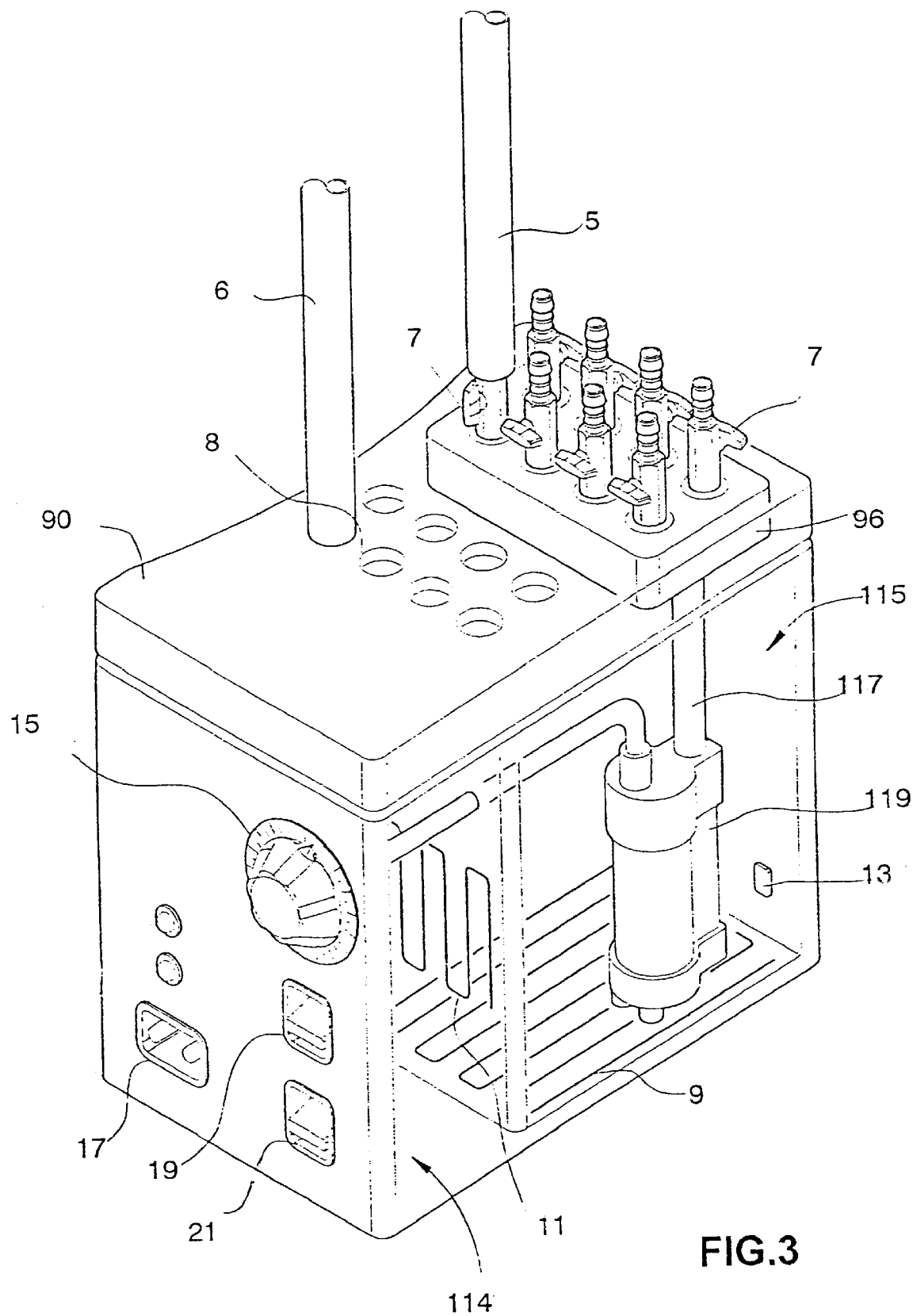
FIG. 3 shows a supply device according to the embodiment of FIG. 1.

According to FIG. 3 the supply device 114 comprises a box 115 with open top, which is heat-insulated at the outside and is closed by a cover 90 of the supply device. In the peripheral area the cover of the box 115 provides several holes 8, via which the return flow lines 6 of the cushions can be inserted through the cover, so that they can directly empty into the box 115. At the bottom side of the cover 90 a supply chamber 96 is formed with supply connections with built-in shut-off valves 7 projecting at the top. The supply chamber 96 is connected to an electrical submergible pump 119 via a connection hose 117, the pump is arranged in the box 115. The bottom side of the box 115 comprises a heating coil, which is operated electrically. Further a cooling coil 11 is provided, which here is only shown at one wall of the box 115, but preferably is arranged at several walls. The supply device 114 further comprises a temperature sensor 13 at the inside of the box 115, an adjustable thermostat 15, an electric supply 17 for charging a storage battery arranged in the supply device 114 outside the box 115 as well as switches 19 and 21 respectively for switching on and off the heating and cooling devices. Outside the box 115 the supply device 114 comprises a refrigerator, which is not shown here and either consists of thermoelectric cells or a mechanical refrigerating machine.

FIG. 3 shows a cushion connected to a supply device 114 via a forward and a return flow line 5, 6. The shut-off valve 7 in the supply connection assigned to the forward flow line 5 is completely opened. The other shut-off valves 7 of the supply connections are closed. It is possible to connect another therapy cushion 1 to the supply device 114 without interrupting the temperature regulation operation for the already connected cushion. It is only necessary to insert the return flow line 6 of the additional cushion 1 into a hole 8 of the cover 90 and to put the forward flow line 5 on a free supply connection and then open it by using the shut-off valve 7. Depending on the size of the respective connected cushion the shut-off valve is opened more or less. Due to the metering function of the shut-off valves the flow rates in the respective cushions 1 can be chosen individually.

The coupling device 10 shown in the FIGS. 4–16 is especially user friendly, because with only one coupling action the forward flow line 5 as well as the return flow line 6 can be connected to the supply device 114, whereby simultaneously the shut-off valves in the supply connection 14 as well as in the coupling part 12 of the double hose 20 are opened. In an uncoupled state of the coupling device 10 these shut-off valves are closed, thus the liquid can neither run out of the supply connection 14 nor out of the coupling part 12. This coupling device 10 is extraordinarily safe, prevents the exchange of the forward and return flow lines 5, 6 and can—according to one embodiment—also be used for other applications, i.e. for forwarding and returning of the patients' blood during dialysis.

The coupling device 10 consists of the coupling part 12 and the supply connection 14. The coupling part 12 has a head 16 and a bottom 18. The head 16 comprises a flanged bushing, wherein a outer hose 22 of a double hose 20 is sealingly haltered by a clamping socket 26. An inner hose 24 penetrates the clamping socket 26 with radial distance. The forward flow line 5 (FIG. 2) is formed by the inner hose 24. The return flow line 6 is formed within the annular chamber between outer hose 22 and inner hose 24. The bottom 18 has a coaxial central chamber 28 and two additional cylindrical chambers 30 with smaller cross-sections, which are diametrically offset one from another and from the main axis. In all three chambers 28, 30 there are arranged shut-off valves, which comprise valve bodies 32 resp. 36 and springs 34 resp. 38. Both springs are supported at their backsides at supporting bodies 40 resp. 42 with rings of ports. A flanged bushing 44 is pressed into the tops of the central chambers 28 and the inner hose 24 sits thereon. Due to the duality of the coupling part 12 mounting of the double hose 20 is very easy, because the outer hose 22 is sealingly clamped in the head 16 and the inner hose 24 is extracted a bit from the outer hose 22 before mounting of the parts, what becomes possible due to it's spiral hose embodiment and then is put onto the flanged bushing 44 and gets centered via pushing together the head 16 and the bottom 18.

The bottom 18 has an upper circular cylindrical peripheral surface 46, which forms a clamping fit together with the inner peripheral surface 48 of the head. After compressing both parts 16, 18 the coupling part 12 is sealed.

Just about in a central region the bottom 18 comprises an outer annular flange 50 joined by a lower peripheral surface 52 with an elliptic or oval contour. This peripheral surface 52 is closed by an end face 54, so that it shows a pot-like construction. The three chambers 28, 30 comprise orifices in this end face 54, which are constructed as valve seats for the valve bodies 32, 36. An O-ring 56 is arranged near the bottom end of this peripheral surface 52.

The supply connection 14 is formed as a counter coupling with a circular cylindrical outer surface 58 and locking projections 60 radially associated in outward direction and extending in upward direction. Inside the supply connection 14 is a cylindrical recess with a peripheral surface 62, which is complementary to the outer peripheral surface 52 of the bottom 18 of the coupling part 12. In the embodiment this recess has an elliptic contour. This recess ends in an end face 64, at which a central channel 68 arranged in a tube 66 as well as two additional radially diametrically offset channels 70 formed as rings of ports do open. The central channel 68 comprises a valve body 72 with a sealing ring and a spring 74, which parts form a shut-off valve. The orifice of the central channel 68 in the end face 64 is surrounded by an open annular groove, wherein an O-ring 76 is inserted. From a valve body 72 a tappet 78 projects coaxially upward into a cavitiy surrounded by the peripheral surface 62. Both valve bodies 36 of the coupling part 12 comprise downwardly directed tappets 80.

Figure 8:
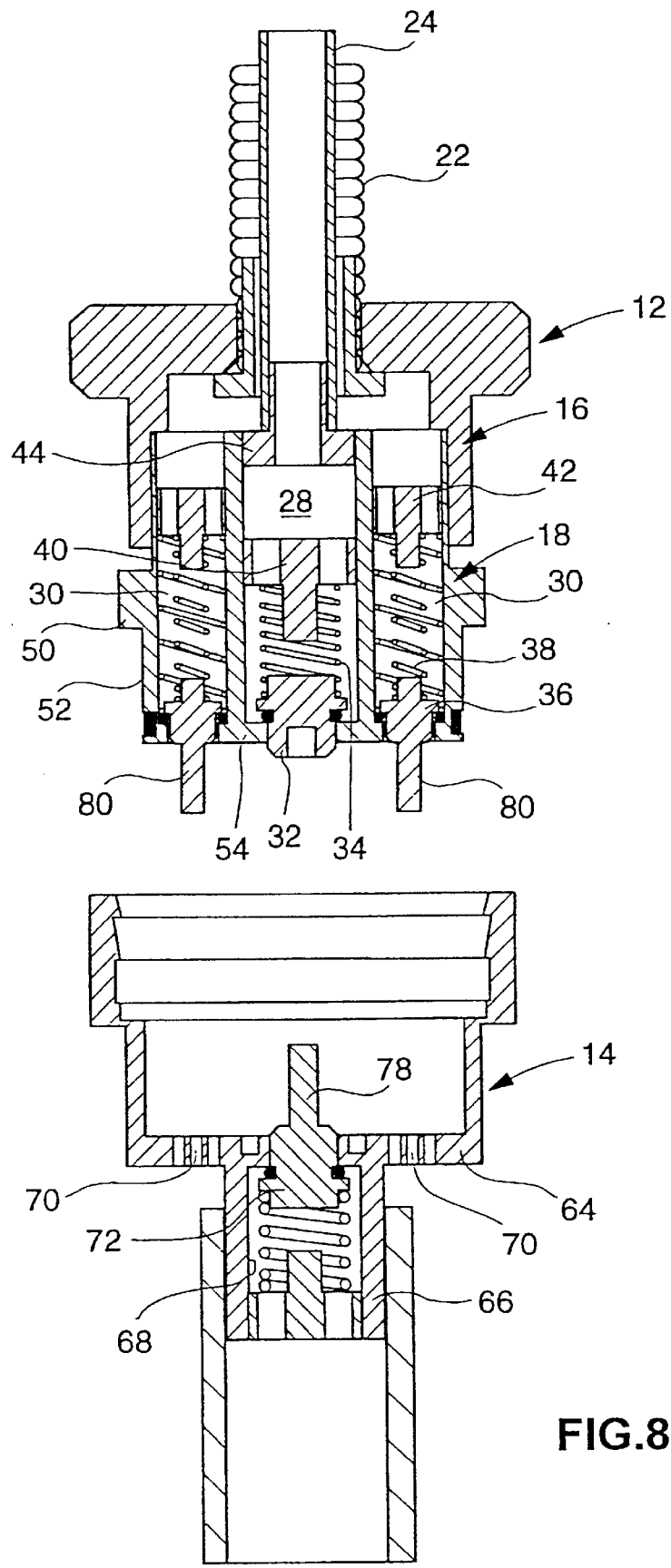
FIG. 8 shows the coupling device according to FIG. 4 in uncoupled state, whereby the shut-off valves of the coupling parts are in closed positions.
Figure 9:
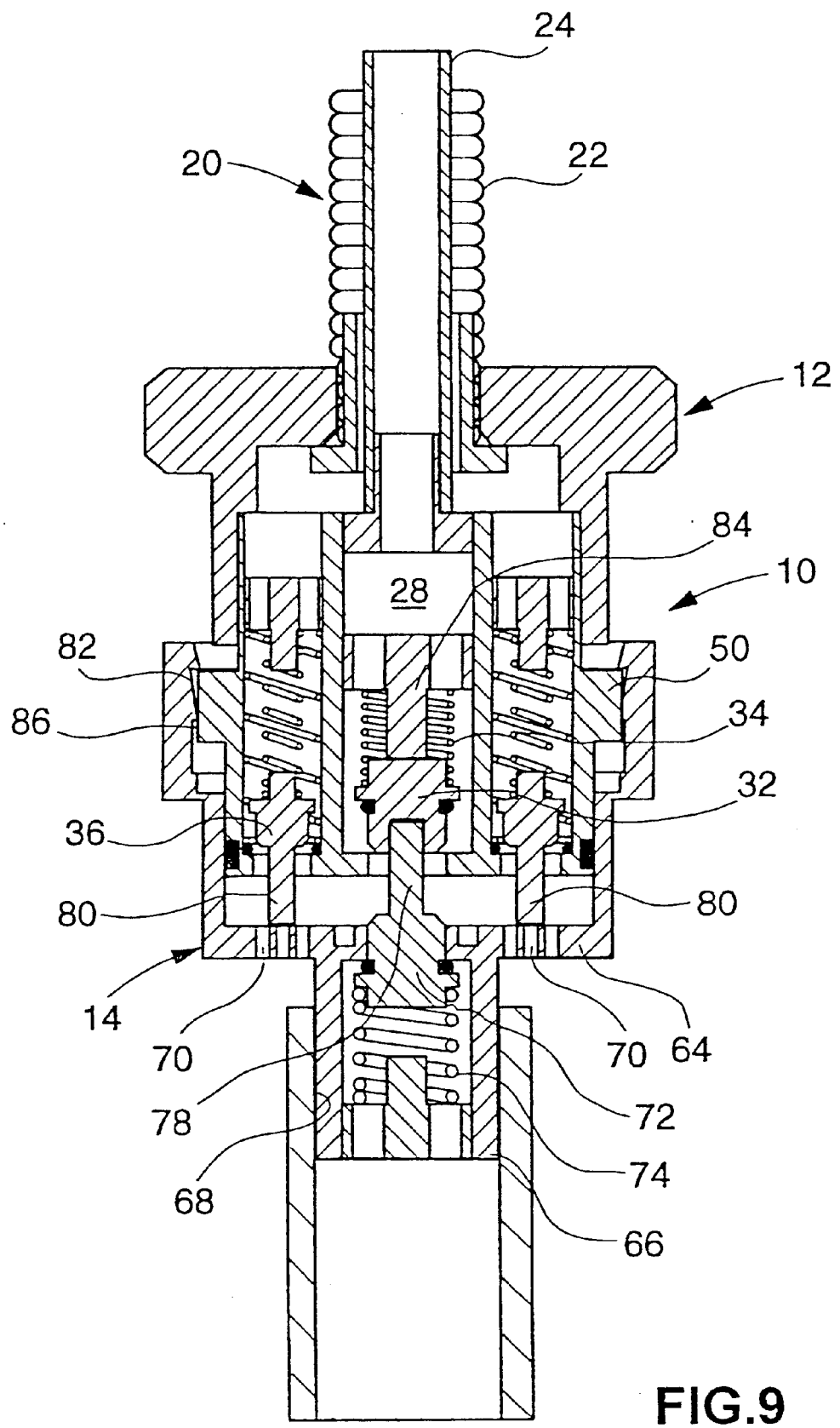
FIG. 9 shows the coupling device according to FIG. 4 in a partly coupled state, whereby individual valves are opened, but at least one main valve is closed.
Figure 10:
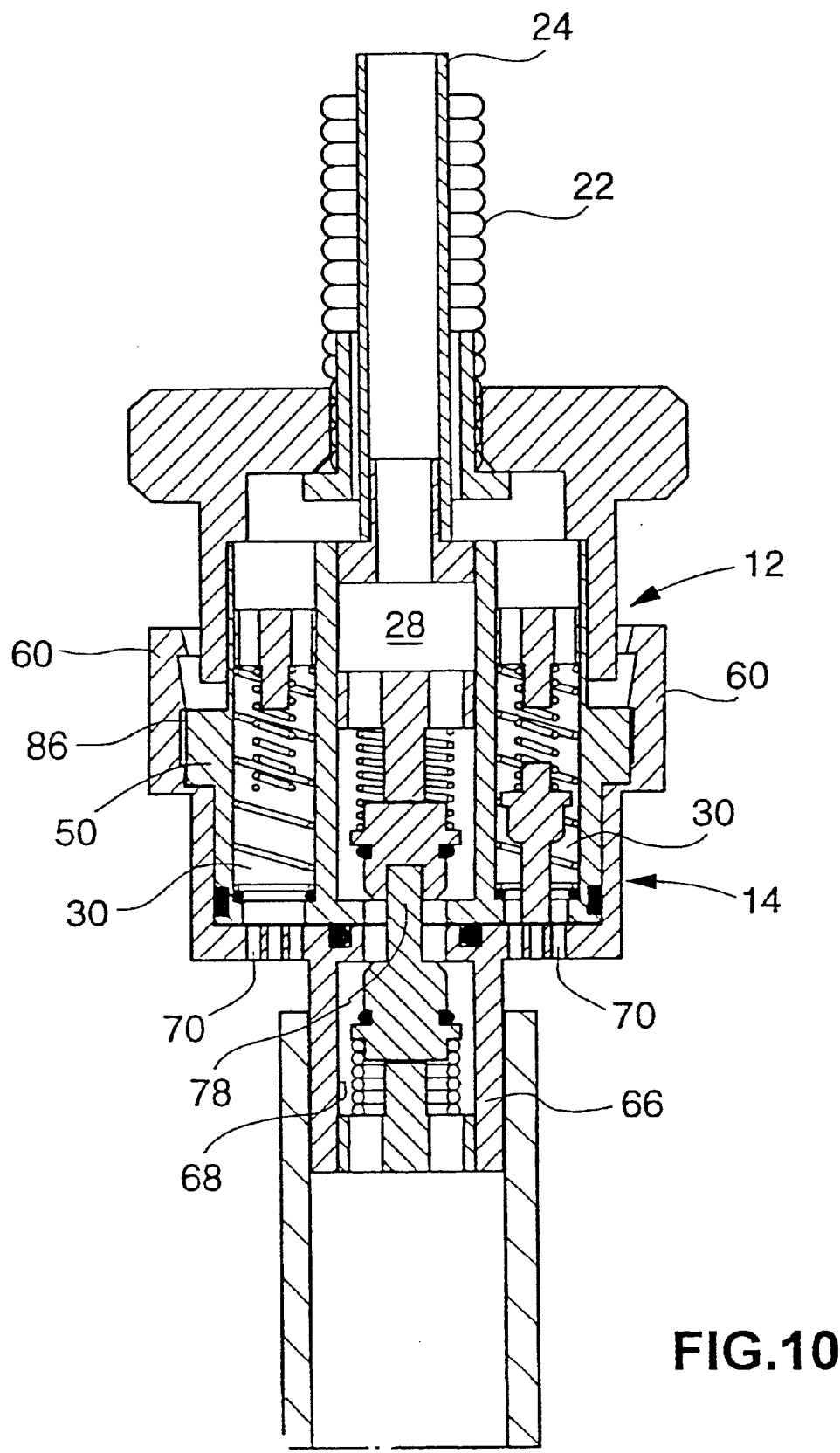
FIG. 10 shows the coupling device in completely coupled state, whereby all valves are open.
Figure 12:
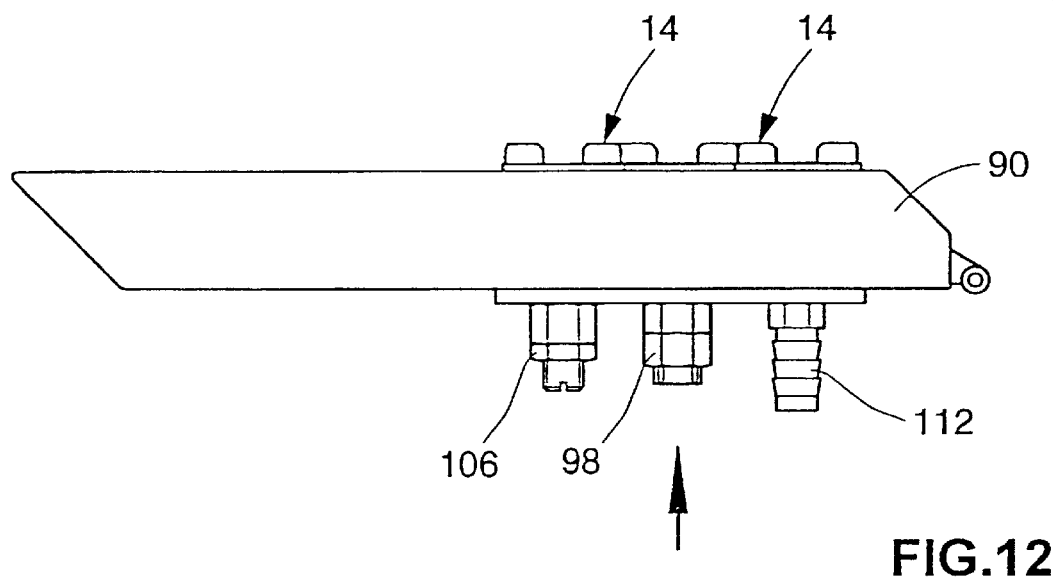
FIG. 12 is a side view of the cover according to FIG. 11.
Figure 11:
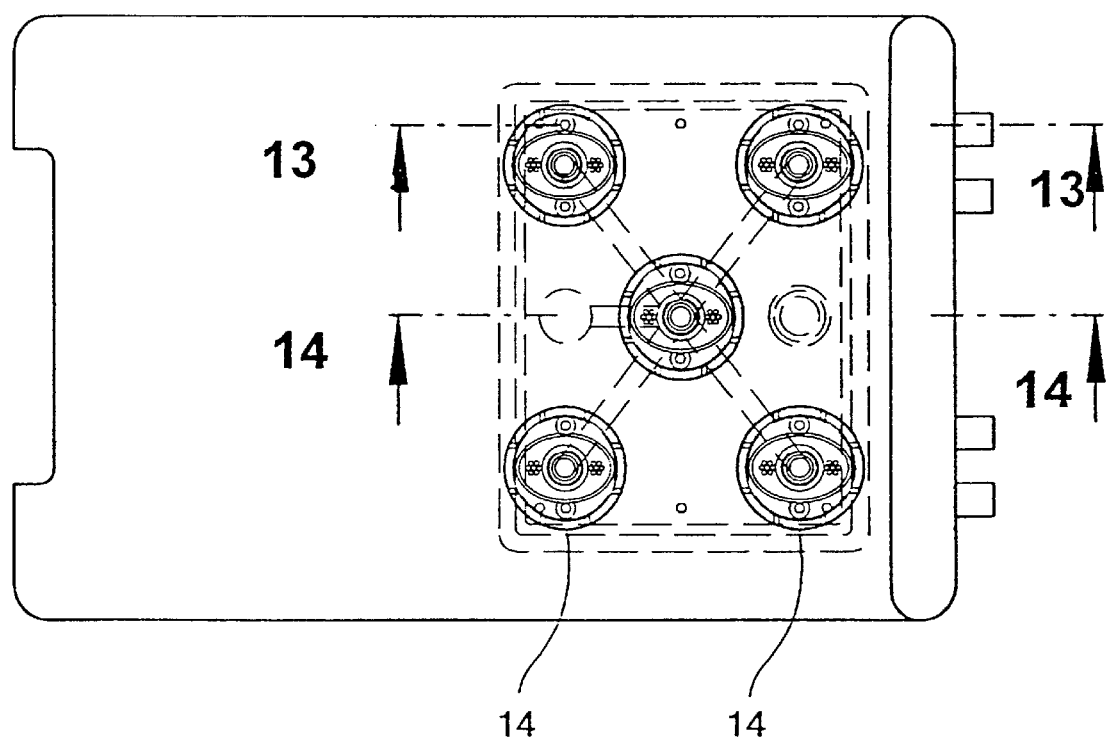
FIG. 11 is a plan view of the cover of the supply device with five supply connections.
Figure 15:
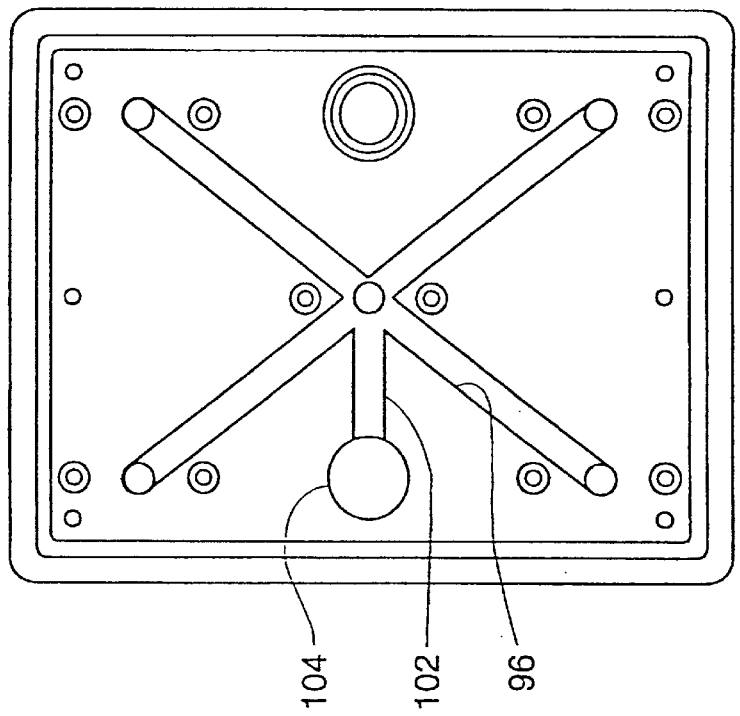
FIG. 15 is a bottom view of an insert fixed to the inside of the cover and FIG. 16 is a explosive representation of the mounting parts for the supply chamber, which are fixed at the cover of the supply device.
Figure 13:
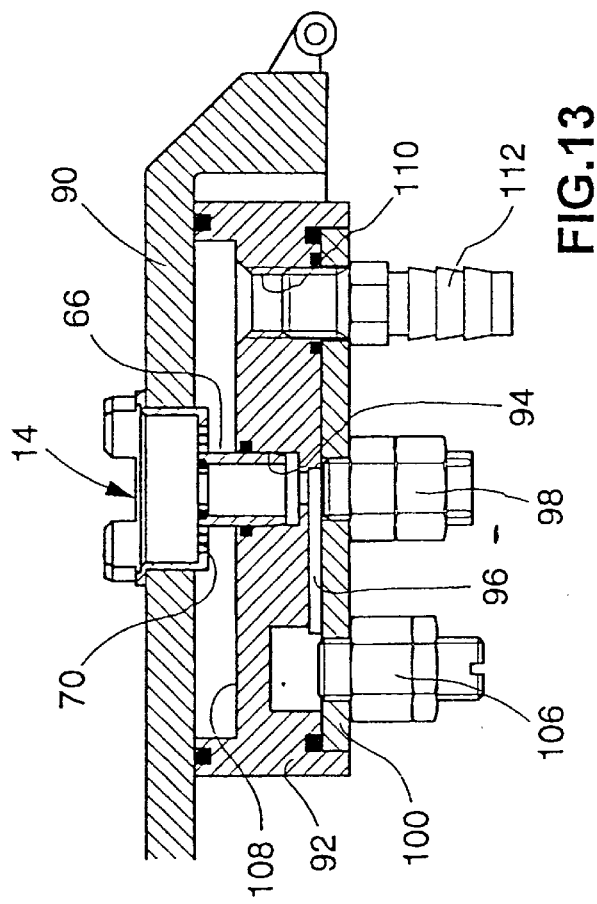
FIG. 13 is a longitudinal sectional view through the cover along line 13—13 of FIG. 11.

In an uncoupled position according to FIG. 8 the shut-off valves in the coupling part 12 and in the supply connection 14 are closed. When the coupling part 12 is inserted into the supply connection, whereby due to the elliptic peripheral surfaces 52, 62 only two defined angle positions do exist, the O-ring 56 at the coupling part 12 at first seals the elliptically shaped chamber of the supply connection 14. During further inserting at the coupling part, the tappets 80 contact the end face 64 and the tappet 78 slides into a frontside feed hole of the valve body 32. An additional short slide stroke of the coupling part 12 causes the shut-off valves to open ba means of the valve bodies 32, 36 of the coupling part 12. This state is shown in FIG. 9. During this the peripheral flange 50 maps into a first locking step of the upward locking projections 60. Because of the spring 74 in the central channel 68 of the supply connection 14 being stronger than the spring 34 in the central chamber 28 of the coupling part 12, the valve body 72 in the central channel 68 remains in closed position and the valve body 32 in the central chamber 28 of the coupling part 12 supports itself at a lift stop tappet 84. Liquid now can run out from the inner hose 24 and the annular chamber between inner hose 24 and outer hose 22 via the channels 70. Caused by further inserting of the coupling part 12 the valve body 72 is lifted from the valve seat, so that the pressurized liquid can flow through the central channel 68 of the supply connection 14 into the central chamber 28 of the coupling part 12. In coupling position the flange 50 maps into a second locking step 86 at the upward locking projections 60. This position is shown in FIG. 10. The central chamber 28 is axially aligned with the central channel 68 in the main axis of the coupling device and both additional chambers 30 in the coupling part 12 are also axially aligned with the additional channels 70.

As shown by the FIGS. 11–16 the supply device 114 has a cover 90, into which five supply connections 14 are inserted from outside and from the bottom of the cover 90 an insert 92 is fixed with an inlayed roundabout seal at the frontside, comprising a plurality of bores 94, into which the tubes 66 of the five supply connections 14 sealingly project due to inlayed O-rings. The five bores 94 are connected to a bottomside groove system forming a supply chamber 96, which is communicating with a central hose connection 98 screwn onto a cover plate 100, which is closing the supply chamber 96 in the insert 92. The supply chamber 96 comprises a branch groove 102, which is leading to a chamber 104 communicating with a safety valve 106, which is haltered in the cover plate 100. The insert 92 comprises a pocket 108 at the side assigned to the cover 90, which is covering all five supply connections 14 and in which the channels 70 of the supply connections 14 can freely discharge. A hose fitting 112 projecting a respective bore in the coverplate 100 is screwed into a draining bore 110 of the insert 92.

Figure 14:
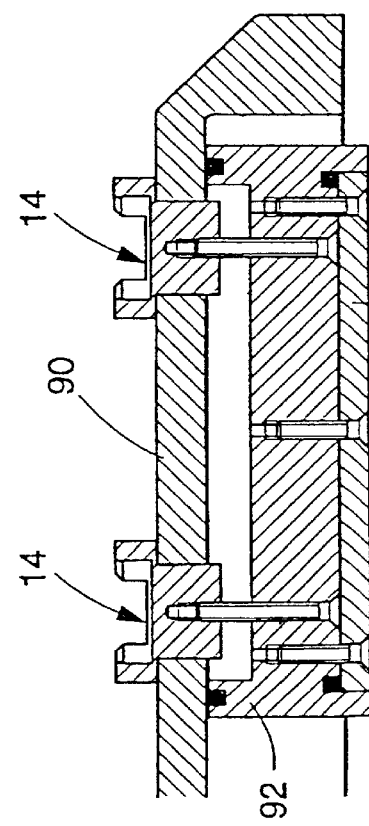
FIG. 14 is a longitudinal sectional view through the cover along line 14—14 of FIG. 11.
Figure 16:
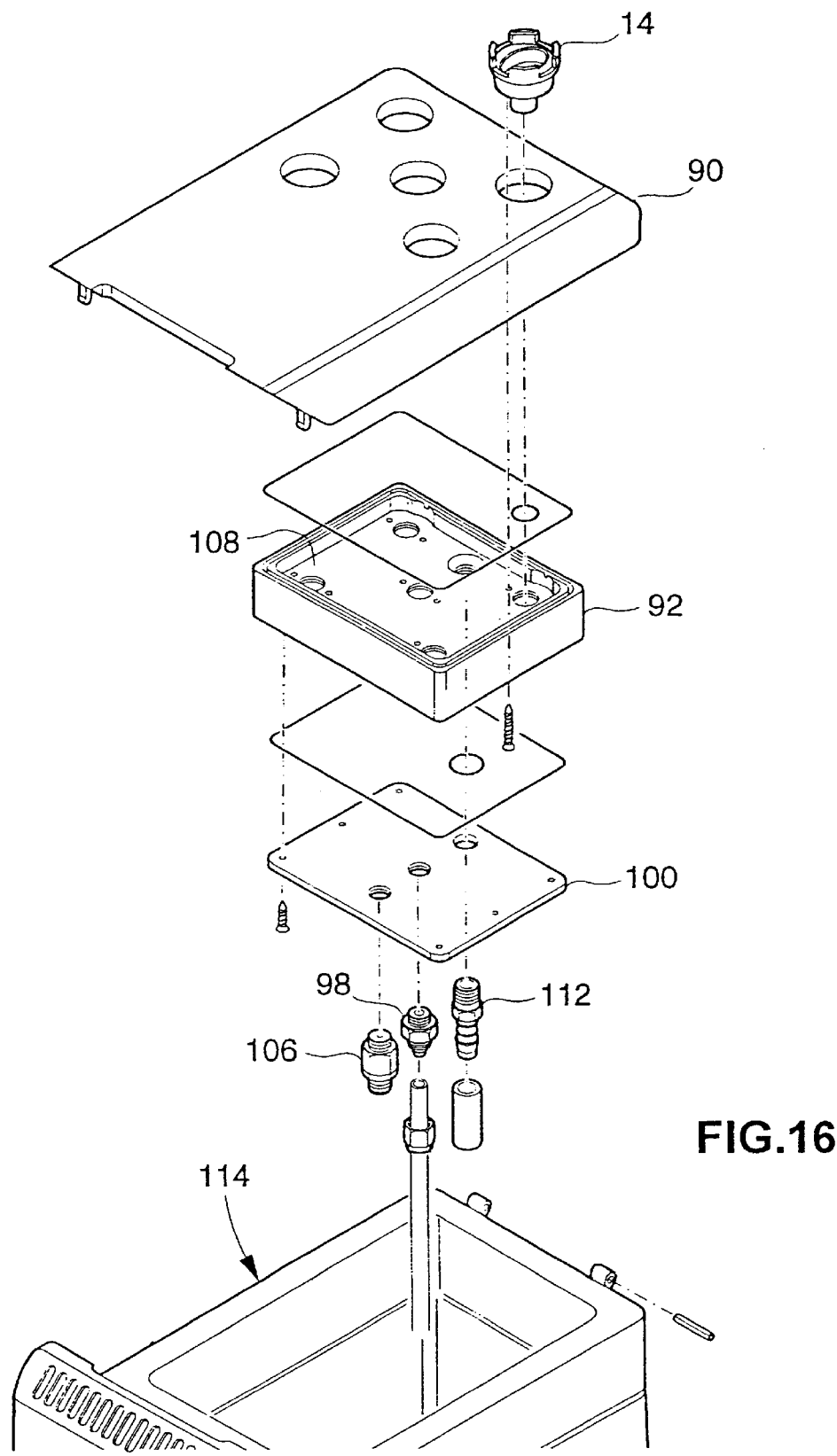

FIG. 14 shows, that the insert 92 is fixed to the cover 90 via two long screws at each of the five supply connections 14 and the cover plate 100 is screwed to the insert 92 via six shorter edge screws. A hose 117 coming from the pressure side of the pump 119 is connected to the central connection 98 and a respective hose, which is stuck on the fitting 112 leads back to the box 115.

In the drawings the supply connections 14 are shown with simple discharge channels 70, because these can discharge into the common pocket 108 in the insert 92. It is understood that the supply connection 14 can also be embodied according to the coupling part 12 for the connection with a double hose 20. In this embodiment the supply connection 14 also comprises a head 16 and a bottom 18 and instead of the channels 70 there are valve chambers 30 as in the coupling part 12. After drawing off the coupling part 12 from the supply connection 14 the additional shut-off valves in the supply connection close, so that no liquid can discharge from both double hoses 20, to be connected.

The inventory coupling device makes possible, that the coupling part 12 can be drawn off the supply connection 14, whereby the shut-off valves close automatically before the sealing between both coupling parts is released. When, according to the embodiment, the supply connection is located in the cover 90 of the supply device 114, the remaining liquid can discharge from the supply connection into the box 115, thus no liquid gets lost. Opening of the shut-off valves is only effected when the coupling part 12 is in it's defined coupling position. Misoperations are prevented. The shut-off valve in the supply connection 14 is opened during the last step of the inserting movement of the coupling part 12. Due to that a two-step-operation is carried out that way, that in the first coupling step both coupling parts 12, 14 are tightly connected to one another and the shut-off valves in the coupling part 12 are opened, so that a discharging of the forward and return flow lines 5, 6 inclusive the stock water in the cushion 1 is possible. Then, in the following second coupling step, the pressurized supply chamber 96 is connected to the forward flow line 5.

The not circular form of the coupling device facilitates a modification to the embodiment shown in the drawings, comprising two chambers 28, 30 of same size in the different halves of the coupling part 12. The embodiment shown with a central chamber 28 and two smaller side chambers 30 in the coupling part 12 also makes possible a circular cylindrical shape of the peripheral sufaces of the coupling part 12 and the supply connection 14 just like that. Then it is advantageous to have a axial alignment of the coupling part 12 in the supply connection 14, i.e. via axial ribs and grooves, so that the coupling motion is only possible in one or at most two turning positions which have to be spaced by 180°. At the end of the inserting motion the axial alignment should be neutralized, so that the coupling part 12 can be rotated into the final coupling position for i.e. 45° or 90°. Due to this at the same time the coupling parts are interlocked and it is ensured that the coupling position is really reached. This rotational movement of the coupling part 12 can be effected on a helical path with little pitch, so that the coupling parts are haltered together with sufficiently high axial tightening force.

I claim:

1. A coupling device for connecting a medical therapy device to a supply device, comprising a coupling part connected to a first line having an inner hose and an outer hose and a counter-coupling connected to a second line, the coupling part featuring a geometrical main axis, the coupling part having a first cylindrical peripheral surface at a leading end thereof and the counter-coupling having a second peripheral surface complementarily designed to the first peripheral surface and an O-ring arranged at one of the peripheral surfaces, the coupling part comprising at least two cylindrical chambers, said chambers having axes parallel with the main axis and provided with openings at one end face of the coupling part respectively, one of the chambers connected to the inner hose of the first line and the at least one further chamber connected to an annular chamber formed between the inner hose and the outer hose, the counter-coupling having at least two channels arranged parallel with the main axis and in the coupling position of the coupling part communicating with one of the chambers of the coupling part respectively via flow paths sealed one against another, the counter-coupling having a second end face perpendicular to the second peripheral surface thereof, the channels having openings at the second end face, the openings of the channels being coaxial to the openings of the chambers of the coupling part in the coupling position thereof, and a second O-ring arranged at one of the end faces of the coupling part and the counter-coupling surrounding the respective opening and in the coupling position being in contact with the respective other one of the end faces of the coupling part and the counter-coupling, a shut-off valve arranged in at least one of the channels of the counter-coupling, the shut-off valve comprising a valve body and a spring pre-stressing the valve body into a closed position thereof, a first tappet provided at one part comprising the coupling part and the valve body of the counter-coupling, the tappet in the coupling position of the coupling part resting on the other one of these parts respectively and holding the valve body in an open position, a spring-actuated second shut-off valve arranged in each one of said chambers, the second shut-off valve comprising a second valve body which in release position of the coupling part closing the opening of the respective chamber, a second tappet oriented parallel with the main axis assigned to the second valve body, the second tappet in the coupling position of the coupling part being supported at the counter-coupling and holding the respective shut-off valve of the chamber in an open position, so that a three-step inserting mode of the coupling part is achieved, whereby firstly the inner spaces of the coupling part and of the counter-coupling are sealed against the surrounding, then the shut-off valves of the chambers are opened and at last the shut-off valve provided in the at least one channel of the counter-coupling is opened.

2. A coupling device as claimed in claim 1, wherein the first tappet is arranged at the valve body of the first shut-off valve provided in the at least one channel and projects axially in the direction of the valve body of the second shut-off valve in one of the chambers of the coupling part, wherein lift stop means are provided for at least one of the valve bodies and wherein during the coupling action of the coupling part the tappet opens the second shut-off valve in the chamber and presses the valve body of the second shut-off valve against the lift stop means and thereafter moves the valve body of the first shut-off valve of the counter-coupling in an open position, whereby the springs for both valve bodies are differing in strength and the weaker spring is assigned to the second shut-off valve provided with the lift stop means.

3. A coupling device as claimed in claim 1, wherein the peripheral surfaces of the coupling part and the counter-coupling have non-circular contours comprising oval and elliptic forms.

4. A coupling device as claimed in claim 1, wherein both chambers and the channels axially aligned with them respectively have at least approximately equal cross-sections respectively and are arranged in different halves of the coupling part and the counter-coupling.

5. A coupling device as claimed in claim 1, wherein one chamber of the coupling part and one channel of the counter-coupling are coaxially arranged to the main axis respectively and wherein the coupling part has at least two further chambers having smaller cross-sections and parallel axes, the axes having equal spacings from the main axis and being circumferentially offset one from another.

6. A coupling device as claimed in claim 1, wherein one shut-off valve is assigned to each opening of all chambers and to each opening of all channels respectively and wherein the spring powers of the springs for the valve bodies of the shut-off valves are selected with respect to one another such that a stepwise coupling action takes place and whereby in an intermediate position of the coupling part, in which the adjacent end faces of the coupling part and the counter-coupling are spaced one from another, at least one chamber of the coupling part communicates with a channel of the counter-coupling while another chamber of the coupling part is shut-off from the channel assigned to it.

7. A coupling device as claimed in claim 1, wherein a supply chamber is formed in an insert of the supply device at the inside of an outer wall comprising the cover, wherein a plurality of counter-couplings are connected to the supply chamber, a plurality of parallel bores are provided in the insert, a tube centrally arranged at each counter-coupling tightly projects into the bores respectively and contains one of the channels with the first shut-off valves respectively, wherein all bores are connected to a common hose connection provided at the inside of the insert by a channel system formed in the insert, whereby the channel system forms the supply chamber, wherein the insert has a flat pocket (108) at it's side facing the outer wall, the tubes of the counter-coupling leading through the flat pocket, and all channels of the counter-coupling but without those channels provided in the tubes freely open in the pocket, and wherein a draining bore extends through the insert and opens in the pocket.

\* \* \* \* \*